(12) United States Patent
Tsubokura et al.

(10) Patent No.: US 7,745,170 B2
(45) Date of Patent: Jun. 29, 2010

(54) PROCESS FOR PRODUCING CAROTENOID COMPOUND

(75) Inventors: Akira Tsubokura, Yokohama (JP); Hisashi Yoneda, Yokohama (JP); Kazuaki Hirasawa, Yokohama (JP)

(73) Assignee: Nippon Oil Corporation, Tokyo (JP)

( * ) Notice: Subject to any disclaimer, the term of this patent is extended or adjusted under 35 U.S.C. 154(b) by 439 days.

(21) Appl. No.: 10/571,902

(22) PCT Filed: Sep. 8, 2004

(86) PCT No.: PCT/JP2004/013033
§ 371 (c)(1), (2), (4) Date: Mar. 14, 2006

(87) PCT Pub. No.: WO2005/028661
PCT Pub. Date: Mar. 31, 2005

(65) Prior Publication Data
US 2007/0105189 A1    May 10, 2007

(30) Foreign Application Priority Data

| Sep. 17, 2003 | (JP) | ............................. 2003-325104 |
| Sep. 17, 2003 | (JP) | ............................. 2003-325130 |
| Sep. 17, 2003 | (JP) | ............................. 2003-325144 |

(51) Int. Cl.
*C12P 23/00* (2006.01)

(52) U.S. Cl. ...................................... 435/67; 435/252.1

(58) Field of Classification Search ...................... None
See application file for complete search history.

(56) References Cited

U.S. PATENT DOCUMENTS

| 3,841,967 | A | | 10/1974 | Dasek et al. |
| 5,360,730 | A | | 11/1994 | Orndorff et al. |
| 5,607,839 | A | | 3/1997 | Tsubokura et al. |
| 5,858,761 | A | * | 1/1999 | Tsubokura et al. ....... 435/252.1 |
| 5,935,808 | A | | 8/1999 | Hirschberg et al. |
| 6,706,278 | B1 | | 3/2004 | Tsubokura et al. |
| 6,825,002 | B2 | * | 11/2004 | Tsubokura et al. ............ 435/67 |
| 2003/0044886 | A1 | | 3/2003 | Tsubokura et al. |

FOREIGN PATENT DOCUMENTS

| JP | 8-9964 | 1/1996 |
| JP | 9-308481 | 12/1997 |
| JP | 2001-095500 A | 4/2001 |
| JP | 2001-512030 A | 8/2001 |
| JP | 2003-304875 | 10/2003 |
| WO | 99/06586 | 2/1999 |

OTHER PUBLICATIONS

Tsubokura A., et al., "*Paracoccus carotinifaciens* sp. nov., a new aerobic gramnegative astaxanthin-producing bacterium" Int. J. Syst. Bacteriol., 199, Vo. 49 No. 1. p. 277-82.

Harkwe M., et al., "*Paracoccus marcusii* sp. nov., an orange gram-negative coccus." Int. J. Syst. Bacteriol., 1998 vol. 48 No. 2 p. 543-8.

Tripathe U., et al., "Studies on *Haematoccocus pluvialis* for improved production of astaxanthin by mutagenesis", World Journal of Microbiology & Biotechnology, 2001, vol. 17, No. 2, pp. 143 to 148.

Eon Seon Jin et al. "A Mutant of the Green Alga *Dunaliella salina* Constitutively Accumulates Zeaxanthin Under All Growth Conditions"; Biotechnology and Bioengineering; vol. 81, No. 1, pp. 115-124; Jan. 5, 2003. (Cited in European Search Report of Sep. 2, 2009 for corresponding EP Application 04787716).

* cited by examiner

*Primary Examiner*—Irene Marx
(74) *Attorney, Agent, or Firm*—Marvin A. Motsenbocker; Mots Law, PLLC

(57) ABSTRACT

The present invention relates to a process for producing zeaxanthin, β-carotene, or lycopene, comprising inducing mutation in a carotenoid-producing microorganism in which the base sequence of DNA corresponding to 16S ribosomal RNA is substantially homologous to the base sequence described in SEQ ID NO: 1; screening for a mutant strain having a high product proportion of zeaxanthin, β-carotene, or lycopene to the whole production amount of carotenoids to provide a microorganism producing zeaxanthin, β-carotene, or lycopene; culturing the mutant microorganism; and harvesting zeaxanthin, β-carotene, lycopene or a carotenoid mixture containing the same from the resultant culture.

4 Claims, 5 Drawing Sheets

Fig. 2

<110> Nippon Oil Corporation

<120> Method for producing carotenoid compound

<130> PH-2223PCT-US

<140> US/10/571,902
<141> 2006-03-14

<150> JP2003/325104
<151> 2003-09-17

<150> JP2003/325130
<151> 2003-09-17

<150> JP2003/325144
<151> 2003-09-17

<160> 2

<210> 1
<211> 1452
<212> DNA
<213> Unknown

<220>
<223> Description of unknown organisms : Base sequence of DNA of E-396(F (Fig. 2 CONTINUED)

ERM BP-4283) corresponding to 16S ribosomal RNA

<220>
<221> unsure
<222> (1350)..(1350)
<223> No. 1350 is unidentified

<400> 1

```
agtttgatcc tggctcagaa cgaacgctgg cggcaggctt aacacatgca agtcgagcga   60
gaccttcggg tctagcggcg gacgggtgag taacgcgtgg gaacgtgccc ttctctacgg  120
aatagccccg ggaaactggg agtaataccg tatacgccct ttgggggaaa gatttatcgg  180
agaaggatcg gcccgcgttg gattaggtag ttggtggggt aatggcccac caagccgacg  240
atccatagct ggtttgagag gatgatcagc cacactggga ctgagacacg gcccagactc  300
ctacgggagg cagcagtggg gaatcttaga caatgggggc aaccctgatc tagccatgcc  360
gcgtgagtga tgaaggcctt agggttgtaa agctctttca gctgggaaga taatgacggt  420
accagcagaa gaagccccgg ctaactccgt gccagcagcc gcggtaatac ggaggggggct  480
agcgttgttc ggaattactg ggcgtaaagc gcacgtaggc ggactggaaa gtcagaggtg  540
aaatcccagg gctcaacctt ggaactgcct ttgaaactat cagtctggag ttcgagagag  600
gtgagtggaa ttccgagtgt agaggtgaaa ttcgtagata ttcggaggaa caccagtggc  660
gaaggcggct cactggctcg atactgacgc tgaggtgcga aagcgtgggg agcaaacagg  720
attagatacc ctggtagtcc acgccgtaaa cgatgaatgc cagacgtcgg caagcatgct  780
tgtcggtgtc acacctaacg gattaagcat tccgcctggg gagtacggtc gcaagattaa  840
aactcaaagg aattgacggg ggcccgcaca agcggtggag catgtggttt aattcgaagc  900
aacgcgcaga accttaccaa cccttgacat ggcaggaccg ctggagagat tcagctttct  960
cgtaagagac ctgcacacag gtgctgcatg gctgtcgtca gctcgtgtcg tgagatgttc 1020
ggttaagtcc ggcaacgagc gcaacccacg tccctagttg ccagcaattc agttgggaac 1080
tctatggaaa ctgccgatga taagtcggag gaaggtgtgg atgacgtcaa gtcctcatgg 1140
```

(Fig. 2 CONTINUED)

```
gccttacggg ttgggctaca cacgtgctac aatggtggtg acagtgggtt aatccccaaa 1200
agccatctca gttcggattg tcctctgcaa ctcgagggca tgaagttgga atcgctagta 1260
atcgcggaac agcatgccgc ggtgaatacg ttcccgggcc ttgtacacac cgcccgtcac 1320
accatgggag ttggttctac ccgacgacgn tgcgctaacc ttcggggggc aggcggccac 1380
ggtaggatca gcgactgggg tgaagtcgta acaaggtagc cgtaggggaa cctgcggctg 1440
gatcacctcc tt                                                    1452

<210> 2
<211> 1426
<212> DNA
<213> Unknown

<220>
<223> Description of unknown organisms : Base sequence of DNA of A-581-1
(FERM BP-4671) corresponding to 16S ribosomal RNA <400> 2
tagagtttga tcctggctca gaacgaacgc tggcggcagg cttaacacat gcaagtcgag 60
cgagaccttc gggtctagcg gcggacgggt gagtaacgcg tgggaacgtg cccttctcta 120
cggaatagcc ccgggaaact gggagtaata ccgtatacgc cctttggggg aaagatttat 180
cggagaagga tcggcccgcg ttggattagg tagttggtga ggtaacggct caccaagccg 240
acgatccata gctggtttga gaggatgatc agccacactg ggactgagac acggcccaga 300
ctcctacggg aggcagcagt ggggaatctt agacaatggg ggcaaccctg atctagccat 360
gccgcgtgag tgatgaaggc cttagggttg taaagctctt tcagctggga agataatgac 420
ggtaccagca gaagaagccc cggctaactc cgtgccagca gccgcggtaa tacggagggg 480
gctagcgttg ttcggaatta ctgggcgtaa agcgcacgta ggcggactgg aaagtcagag 540
gtgaaatccc agggctcaac cttggaactg cctttgaaac tatcagtctg gagttcgaga 600
gaggtgagtg gaattccgag tgtagaggtg aaattcgtag atattcggag gaacaccagt 660
ggcgaaggcg gctcactggc tcgatactga cgctgaggtg cgaaagcgtg gggagcaaac 720
```

(Fig. 2 CONTINUED)

```
aggattagat accctggtag tccacgccgt aaacgatgaa tgccagacgt cggcaagcat 780
gcttgtcggt gtcacaccta acggattaag cattccgcct ggggagtacg gtcgcaagat 840
taaaactcaa aggaattgac gggggcccgc acaagcggtg gagcatgtgg tttaattcga 900
agcaacgcgc agaaccttac caacccttga catggcagga ccgctggaga gattcagctt 960
tctcgtaaga gacctgcaca caggtgctgc atggctgtcg tcagctcgtg tcgtgagatg 1020
ttcggttaag tccggcaacg agcgcaaccc acgtccctag ttgccagcat tcagttgggc 1080
actctatgga aactgccggt gataagccgg aggaaggtgt ggatgacgtc aagtcctcat 1140
ggcccttacg ggttgggcta cacacgtgct acaatggtgg tgacagtggg ttaatcccca 1200
aaagccatct cagttcggat tgtcctctgc aactcgaggg catgaagttg gaatcgctag 1260
taatcgcgga acagcatgcc gcggtgaata cgttcccggg ccttgtacac accgcccgtc 1320
acaccatggg agttggttct acccgacgac gctgcgctaa cccttcgggg aggcaggcgg 1380
ccacggtagg atcagcgact ggggtgaagt cgtaacaagg tagcca            1426
```

PROCESS FOR PRODUCING CAROTENOID COMPOUND

TECHNICAL FIELD

The present invention relates to a microbial process for producing zeaxanthin, β-carotene, lycopene, or a carotenoid mixture thereof, useful as natural yellow pigment, natural red pigment, or antioxidant for feed, food, cosmetics, pharmaceuticals, and the like.

BACKGROUND ART

Zeaxanthin is contained in various plants such as corn, added to feed as natural yellow pigment, and known to have applications for improving the color tone of egg yolk, meat, or skin of a fowl such as chicken and uses as a coloring agent for food. It also has a potent antioxidant effect (Fisheries Science, 62(1): 134-137, 1996), and has been reported to have an anti-tumor effect (Biol. Pharm. Bull., 18(2): 227-233, 1995). Zeaxanthin is known to be, together with lutein, present in the retina and lens and involved in the maintenance of eye health (FOOD Style 21, 3(3): 50-53, 1999). Due to these physiological effects, zeaxanthin is useful as a health food, cosmetic, or pharmaceutical material. β-Cryptoxanthin is contained in citrus fruits, known to have an anti-tumor effect (Biol. Pharm. Bull., 18(2): 227-233, 1995), and has applications as a food material or a compounding ingredient for feed. β-Carotene has provitamin A and antioxidant actions and is widely used as feed additive, food additive, natural coloring agent, or the like.

Known as a process for producing zeaxanthin are chemical synthesis using, as a raw material, an optically active hydroxyketone obtained by the asymmetric reduction of oxoisophorone (Pure Appl. Chem., 63(1): 45, 1991) and extraction from corn seeds (Seitai Shikiso (Biochrome), 1974, Asakura-shoten). A process by extraction from marigold is also known (JP Patent Publication (Kokai) No. 08-092205 A (1996)); however, a marigold-derived carotenoid mainly comprises lutein and has a reduced content of zeaxanthin. Further, microorganisms for production thereof include *Spirulina* algae (JP Patent Publication (Kokai) No. 10-155430 A (1998)), *Nannochloris* spp. microalgae (JP Patent Publication (Kokai) No. 07-059558 A (1995)), *Flexibacter* spp. bacteria (JP Patent Publication (Kokai) No. 05-328978 A (1993)), *Alteromonas* spp. bacteria (JP Patent Publication (Kokai) No. 05-049497 A (1993)), *Flavobacterium* spp. bacteria (Carotenoids, in Microbial Technology, 2nd edn, Vol. 1, 529-544, New York: Academic Press), *Agrobacterium aurantiacum* (FEMS Microbiology Letters, 128: 139-144, 1995), and a bacterial strain, E-396 (FERM BP-4283) belonging to a novel genus (JP Patent Publication (Kokai) No. 07-079796 A (1995), JP Patent Publication (Kokai) No. 08-009964 A (1996), U.S. Pat. No. 5,607,839, and U.S. Pat. No. 5,858,761).

β-Carotene is a natural yellow carotenoid contained in green and yellow vegetables such as carrot and finds wide use as a coloring agent for foods such as batter and margarine. It also has provitamin A activity and is an important nutrient for human. This substance is known to have an antioxidant effect (Fisheries Science, 62(1): 134-137, 1996) and has been reported to have anti-tumor and anti-cancer effects (Biol. Pharm. Bull., 18(2): 227-233, 1995). Due to these physiological effects, β-carotene is useful not only as a coloring agent, but also as a functional material for use in feed, food, cosmetics, or pharmaceuticals.

Known as a process for producing β-carotene are chemical synthesis from β-ionone (Pure Appl. Chem., 63(1): 45, 1979) and extraction from green and yellow vegetables such as carrot, sweetpotato, and pumpkin (Tennen Chakusyokuryo (Natural Coloring Agents) Handbook, Korin Publishing Co., Ltd., Tennen Chakusyokuryo Handbook Editorial board ed.). In addition, as example of production of β-carotene by a microorganism is known that by *Dunaliella* algae (J. Phycol, 23: 176, 1987), *Blakeslea trispora* (filamentous fungi) (Appl. Environ. MicroBiol. 36: 639-642, 1979), *Phaffia rhodozyma* (yeast) (JP Patent Publication (Kokai) No. 05-168465 A (1993)), *Rhodotorula* spp. yeasts (JP Patent Publication (Kokai) No. 06-022748 A (1994)), *Agrobacterium aurantiacum* (FEMS Microbiology Letters, 128: 139-144, 1995), or the bacterial E-396 strain (FERM BP-4283) belonging to a novel genus (JP Patent Publication (Kokai) No. 07-079796 A (1995), JP Patent Publication (Kokai) No. 08-009964 A (1996), U.S. Pat. No. 5,607,839, and U.S. Pat. No. 5,858,761).

Lycopene is a natural red carotenoid contained in tomato and useful as a coloring agent for food. It also has a potent antioxidant effect (Arch. Biochem. Biophys., 271: 532, 1989), is known to inhibit the oxidation of low density lipoproteins associated with arteriosclerosis (Nutr. Metab. Cordiovasc. Dis 7: 433, 1997) and has been reported to suppress the proliferation of cancer cells (J. Natl. Cancer Inst. 91: 313, 1999). Due to these physiological effects, lycopene is useful as a material for use in feed, food, cosmetics, or pharmaceuticals.

Known as a process for producing lycopene are chemical synthesis using linalool or geraniol as raw material (JP Patent Publication (Kokai) No. 2001-039943 A (2001)) and separation and refinement from tomato (JP Patent Publication (Kokai) No. 2002-193850 A (2002)). In addition, microorganisms for production of lycopene include *Dunaliella* algae (JP Patent Publication (Kokai) No. 2001-161391 A (2001)), *Chlorella* algae (JP Patent Publication (Kokai) No. 2000-152778 A (2000)), and *Rhodobacter* spp. bacteria (JP Patent Publication (Kokai) No. 08-239658 A (1996)). The bacterial E-396 (FERM BP-4283) strain belonging to a novel genus (JP Patent Publication (Kokai) No. 07-079796 A (1995), JP Patent Publication (Kokai) No. 08-009964 A (1996), U.S. Pat. Nos. 5,607,839, and 5,858,761) is also known to produce carotenoid compounds at high concentrations, but the level of lycopene production is minimal.

However, the above-described processes for chemically synthesizing zeaxanthin, β-carotene, and lycopene have problems in terms of safety and the directional trend of recent years toward a natural product because their use of organic solvents. Also, the conventional cultivation using a microorganism is not practical because of low productivity, and extraction from a plant (for example, corn, carrot, tomato, or the like) has the disadvantages of requiring too much cost because of its low content of a desired carotenoid compound and making its stable supply difficult because of weather dependency. The E-396 strain, which is known as a microorganism producing carotenoid compounds, has low product proportions of zeaxanthin, β-carotene, and lycopene to the total carotenoids, although it has provided an established process for producing, at high concentrations on an industrial scale, carotenoid compounds having safety already confirmed by various tests and including astaxanthin.

Thus, there is need for an inexpensive process for producing zeaxanthin, β-carotene, and lycopene with high safety, by which they can be stably supplied.

DISCLOSURE OF THE INVENTION

As a result of intensive studies for solving the above-described problems, the present inventors have discovered that microorganisms producing carotenoid compounds such as astaxanthin may be subjected to mutation treatment to easily provide microorganisms which are high in the product proportions of zeaxanthin, β-carotene, and lycopene to the whole production amount of carotenoids, thereby accomplishing the present invention.

Thus, the present invention provides the following individual inventions.

(1) A process for producing zeaxanthin or a carotenoid mixture containing zeaxanthin, comprising inducing mutation in an astaxanthin-producing microorganism in which the base sequence of DNA corresponding to 16S ribosomal RNA is substantially homologous to the base sequence described in SEQ ID NO: 1; screening for a mutant strain having a higher product proportion (mass %) of zeaxanthin to the whole production amount of carotenoids than the parent strain to provide a zeaxanthin-producing microorganism; culturing the zeaxanthin-producing microorganism; and harvesting zeaxanthin or a carotenoid mixture containing zeaxanthin from the resultant culture.

(2) The process described in invention (1) above wherein the screening for a mutant strain having a higher product proportion (mass %) of zeaxanthin to the whole production amount of carotenoids than the parent strain is a step comprising selecting yellow to orange colonies on a solid medium.

(3) The process described in invention (1) or (2) above wherein the proportion of the zeaxanthin produced by the zeaxanthin-producing microorganism is 20 mass % or more to the whole production amount of carotenoids.

(4) The process described in any of inventions (1) to (3) above wherein the proportion of each of echinenone, 3-hydroxyechinenone, asteroidenone, canthaxanthin, adonirubin, adonixanthin, and astaxanthin produced by the zeaxanthin-producing microorganism is less than 10 mass % to the whole production amount of carotenoids.

(5) The process described in any of inventions (1) to (4) above wherein the carotenoid mixture containing zeaxanthin comprises β-cryptoxanthin and/or β-carotene.

(6) The process described in any of inventions (1) to (5) above wherein the astaxanthin-producing microorganism is selected from a strain, E-396 (FERM BP-4283) and mutant strains thereof, and a strain, A-581-1 (FERM BP-4671) and mutant strains thereof (7) A process for producing β-carotene or a carotenoid mixture containing β-carotene, comprising inducing mutation in a carotenoid-producing microorganism as a parent strain for mutation in which the base sequence of DNA corresponding to 16S ribosomal RNA is substantially homologous to the base sequence described in SEQ ID NO: 1 and which produces at least one carotenoid compound selected from echinenone, β-cryptoxanthin, 3-hydroxyechinenone, asteroidenone, canthaxanthin, zeaxanthin, adonirubin, adonixanthin, and astaxanthin; screening for a mutant strain having a higher product proportion (mass %) of β-carotene to the whole production amount of carotenoids than the parent strain to provide a β-carotene-producing microorganism; culturing the β-carotene-producing microorganism; and harvesting β-carotene or the carotenoid mixture containing β-carotene from the resultant culture.

(8) The process described in invention (7) above, wherein in the process comprises using, as the parent strain for mutation, a carotenoid-producing microorganism for which the proportion of the combined production amount of canthaxanthin and echinenone to the whole production amount of carotenoids is 50 mass % or more.

(9) The process described in invention (7) or (8) above, wherein in the process comprises using, as the parent strain for mutation, a carotenoid-producing microorganism for which the proportion of the combined production amount of zeaxanthin and β-cryptoxanthin to the whole production amount of carotenoids is 50 mass % or more.

(10) The process described in any of inventions (7) to (9) above wherein the screening for a mutant strain having a higher product proportion (mass %) of β-carotene to the whole production amount of carotenoids than the parent strain is a step comprising selecting yellow to orange colonies on a solid medium.

(11) The process described in any of inventions (7) to (10) above wherein the proportion of β-carotene produced by the β-carotene-producing microorganism is 50 mass % or more to the whole production amount of carotenoids.

(12) The process described in any of inventions (7) to (11) above wherein the proportion of each of echinenone, β-cryptoxanthin, 3-hydroxyechinenone, asteroidenone, canthaxanthin, zeaxanthin, adonirubin, adonixanthin, and astaxanthin produced by the β-carotene-producing microorganism is less than 20 mass % to the whole production amount of carotenoids.

(13) The process described in any of inventions (7) to (12) above wherein the carotenoid-producing microorganism is selected from a strain, E-396 (FERM BP-4283) and mutant strains thereof, and a strain, A-581-1 (FERM BP-4671) and mutant strains thereof.

(14) A process for producing lycopene or a carotenoid mixture containing lycopene, comprising inducing mutation in a carotenoid-producing microorganism as a parent strain for mutation, in which the base sequence of DNA corresponding to 16S ribosomal RNA is substantially homologous to the base sequence described in SEQ ID NO: 1 and which produces at least one carotenoid compound selected from β-carotene, echinenone, β-cryptoxanthin, 3-hydroxyechinenone, asteroidenone, canthaxanthin, zeaxanthin, adonirubin, adonixanthin, and astaxanthin; screening for a mutant strain having a higher product proportion (mass %) of lycopene to the whole production amount of carotenoids than the parent strain to provide a lycopene-producing microorganism; culturing the lycopene-producing microorganism; and harvesting lycopene or the carotenoid mixture containing lycopene from the resultant culture.

(15) The process described in invention (14) above wherein the screening for a mutant strain having a higher product proportion (mass %) of lycopene to the whole production amount of carotenoids than the parent strain is a step comprising selecting pink to reddish violet colonies on a solid medium.

(16) The process described in invention (14) or (15) above wherein the proportion of the lycopene produced by the lycopene-producing microorganism is 40 mass % or more to the whole production amount of carotenoids.

(17) The process described in any of inventions (14) to (16) above wherein the proportion of each of β-carotene, echinenone, β-cryptoxanthin, 3-hydroxyechinenone, asteroidenone, canthaxanthin, zeaxanthin, adonirubin, adonixanthin, and astaxanthin produced by the lycopene-producing microorganism is less than 20 mass % to the whole production amount of carotenoids.

(18) The process described in any of inventions (14) to (17) above wherein the carotenoid-producing microorganism is selected from a strain, E-396 (FERM BP-4283) and mutant strains thereof, and a strain, A-581-1 (FERM BP-4671) and mutant strains thereof The present invention is described below in detail.

The process of the invention uses, as parent strains for mutation, microorganisms producing astaxanthin or carotenoid, including an astaxanthin- or carotenoid-producing microorganism in which the base sequence of DNA corresponding to 16S ribosomal RNA is substantially homologous to the base sequence described in SEQ ID NO: 1. As used herein, "substantially homologous" refers to 98% or more homology in consideration of error frequency and the like in DNA sequencing.

Specific examples of the astaxanthin- or carotenoid-producing microorganism which has the sequence substantially homologous to the above described sequence can include a strain, E-396 (FERM BP-4283) and a strain, A-581-1 (FERM BP-4671), and various mutant strains obtained by mutating and modifying the E-396 or A-581-1 strain and related species to these two kinds of strains. The DNA base sequence of SEQ ID NO: 1 corresponds to the ribosomal RNA of the E-396 strain; the DNA base sequence of SEQ ID NO: 2 to the ribosomal RNA of the A-581-1 strain. The homology between the base sequences of 16S ribosomal RNA of the E-396 and A-581-1 strains is 99.4%, demonstrating that they are strains closely related to each other. Thus, these strains form one group as bacteria producing carotenoids. Parent strains for mutation used in the process of the invention are defined as astaxanthin- or carotenoid-producing bacteria which are the E-396 and A-581-1 strains, and mutants of the E-396 or A-581-1 strain and related species of these strains, in which the base sequence of DNA corresponding to 16S ribosomal RNA has 98% or more homology to the base sequence described in SEQ ID NO: 1.

The E-396 strain as an example of the astaxanthin- or carotenoid-producing microorganism used in the invention is described. This strain was newly isolated by the present inventors, and deposited in International Patent Organism Depositary, National Institute of Advanced Industrial Scientific and Technology (Higashi 1-chome 1-banchi 1 chuo dai-6, Tsukuba City, Ibaraki, Japan) under FERM BP-4283 on Apr. 27, 1993. In addition, specific examples of other microorganisms can include the A-581-1 strain. This strain was newly isolated by the present inventors, and deposited in International Patent Organism Depositary, National Institute of Advanced Industrial Scientific and Technology (Higashi 1-chome 1-banchi 1 chuo dai-6, Tsukuba City, Ibaraki, Japan) under FERM BP-4671 on May 20, 1994.

Mutation treatment of the astaxanthin-producing microorganism and selection of a zeaxanthin-producing mutant strain A method for subjecting the astaxanthin-producing microorganism to mutation treatment is not particularly restricted in so far as it induces the mutation thereof For example, chemical methods employing mutagenic agents such as N-methyl-N'-nitro-N-nitrosoguanidine (NTG) and ethyl methanesulfonate (EMS), physical methods such as ultraviolet irradiation and X-ray irradiation, biological methods employing gene recombination, transposon, and the like can be used. The mutation treatment may be carried out at a time, or twice or more e.g. in the manner that the mutation treatment is performed to provide mutants of the astaxanthin-producing microorganism which are further subjected to mutation treatment.

From among the mutants of the astaxanthin-producing microorganism obtained as described above, a mutant strain having a higher product proportion (mass %) of zeaxanthin to the whole production amount of carotenoids than the parent strain is then selected to provide the zeaxanthin-producing microorganism. For this purpose, colonies may be formed on a solid medium after the mutation treatment, followed by randomly selecting colonies, but preferably colonies taking on yellow to orange color are selected in comparison with red to reddish orange colonies of the parent strain for efficiently obtaining the zeaxanthin-producing microorganism (mutant) because colonies of the zeaxanthin-producing microorganism often take on yellow to orange color. The inclusion of this step dramatically improves a probability capable of obtaining a mutation strain having a high product proportion of zeaxanthin to the whole production amount of carotenoids.

The colonies of each mutant strain selected as described above are then cultured using a conventional method, and, after the end of the cultivation, carotenoid compounds contained in the culture solution of each mutant strain are analyzed to select a mutant strain having a high product proportion of zeaxanthin.

The cultivation of the mutant strain can be carried out, for example, in a medium which is necessary for the growth of the producing microorganism and contains ingredients generating carotenoid compounds. The method for cultivation may be any method including shake culture using test tubes, flasks, and the like, aeration agitation culture, or the like. The method for analyzing carotenoid compounds may be any method if it can separate and detect carotenoid compounds; for example, high performance liquid chromatography, thin layer chromatography, or paper chromatography may be used.

According to the present invention, the zeaxanthin-producing microorganism is obtained by screening for a mutant strain having a high product proportion of zeaxanthin based on the whole amount of produced carotenoids; "the whole amount of carotenoids" as used herein refers to the total amount of carotenoids compounds such as astaxanthin, canthaxanthin, adonixanthin, $\beta$-carotene, echinenone, zeaxanthin, $\beta$-cryptoxanthin, 3-hydroxyechinenone, asteroidenone, and adonirubin.

An astaxanthin-producing microorganism like the E-396 strain concurrently produces many kinds of carotenoid compounds such as astaxanthin, canthaxanthin, adonixanthin, $\beta$-carotene, echinenone, zeaxanthin, $\beta$-cryptoxanthin, 3-hydroxyechinenone, asteroidenone, and adonirubin. Thus, the product proportion of zeaxanthin to the whole production amount of carotenoids is low, being usually on the order of 0 to 10 mass %. According to the invention, mutation is induced in an astaxanthin-producing microorganism, followed by screening for a mutant strain having a particularly high product proportion of zeaxanthin to the whole production amount of carotenoids. Criteria for the selection at least require that the product proportion of zeaxanthin after the mutation is higher than that of zeaxanthin in the parent strain; there is selected a mutant strain in which the proportion of the produced zeaxanthin to the whole production amount of carotenoids is preferably 20 mass % or more, more preferably 40 mass % or more, and even more preferably 60 mass % or more.

It is estimated that the biosynthesis of astaxanthin uses upstream $\beta$-carotene, and takes place by modifying the 6-membered rings at both ends thereof employing an enzyme for ketonization and a hydroxylase, respectively (See FIG. 1). Complete deficiency of the enzyme for ketonization is estimated to lead to the production of only β-carotene, β-cryptoxanthin, and zeaxanthin and to provide no production of echinenone, canthaxanthin, 3-hydroxyechinenone, asteroidenone, adonirubin, adonixanthin, and astaxanthin, which require the enzyme for ketonization. Incomplete deficiency of the enzyme for ketonization is estimated to produce decreased proportions of echinenone, canthaxanthin, 3-hydroxyechinenone, asteroidenone, adonirubin, adonixanthin, and astaxanthin based on the whole amount of carotenoids. Thus, as another useful means for selecting the zeaxanthin-producing microorganism from among the mutant strains, a method can be used in which the selection is carried out on the basis of decreased proportions of echinenone, canthaxanthin, 3-hydroxyechinenone, asteroidenone, adonirubin, adonixanthin, and astaxanthin based on the whole amount of carotenoids. The selection may be performed based on that the proportion of each of the above-described compounds to the total carotenoids is less than 10 mass %, preferably less than 5 mass %, and more preferably less than 1 mass %.

Mutation treatment of the carotenoid-producing microorganism and selection of a β-carotene-producing mutant strain The parent strain for mutation as used in the invention is defined as a carotenoid-producing microorganism in which the base sequence of DNA corresponding to 16S ribosomal RNA has 98% or more homology to the base sequence described in SEQ ID NO: 1 and which produces at least one carotenoid compound selected from echinenone, β-cryptoxanthin, 3-hydroxyechinenone, asteroidenone, canthaxanthin, zeaxanthin, adonirubin, adonixanthin, and astaxanthin; preferably, a carotenoid-producing microorganism having a proportion of the combined production amount of canthaxanthin and echinenone to the whole production amount of carotenoids of 50 mass % or more, or a proportion of the combined production amount of zeaxanthin and β-cryptoxanthin to the whole production amount of carotenoids of 50 mass % or more is used. More preferably, a carotenoid-producing microorganism having a proportion of the combined production amount of canthaxanthin and echinenone to the whole production amount of carotenoids of 70 mass % or more, or a proportion of the combined production amount of zeaxanthin and β-cryptoxanthin to the whole production amount of carotenoids of 70 mass % or more is used. As used herein, "the whole amount of carotenoids" refers to the total amount of carotenoids such as β-carotene, echinenone, β-cryptoxanthin, 3-hydroxyechinenone, asteroidenone, canthaxanthin, zeaxanthin, adonirubin, adonixanthin, and astaxanthin.

In the biosynthesis of carotenoids, it is estimated that rings are formed at both ends of lycopene to generate β-carotene whose 6-membered rings at both ends are further modified by an enzyme for ketonization and a hydroxylase, respectively to produce canthaxanthin, zeaxanthin, astaxanthin, and the like (See FIG. 1).

The present inventors have found that a probability capable of obtaining the β-carotene-producing microorganism is dramatically improved by using, as a parent strain for mutation, a microorganism producing canthaxanthin and echinenone at high proportions or a microorganism producing zeaxanthin and β-cryptoxanthin at high proportions, compared to that by using a microorganism producing astaxanthin at a high proportion as a parent strain for mutation. These phenomena can be explained as follows. Although the enzymes for hydrolyzing and ketonizing β-carotene have to be deleted in order to accumulate β-carotene for the carotenoid-producing microorganism producing astaxanthin at a high proportion because the microorganism combines both enzymes, only the enzyme for ketonization has merely to be deleted through mutation for the microorganism producing the total amount of canthaxanthin and echinenone at a high proportion because it has the hydroxylase deleted, or only the hydroxylase has merely to be deleted for the microorganism producing the total amount of zeaxanthin and β-cryptoxanthin at a high proportion because it has the enzyme for ketonization deleted. A microorganism producing the total amount of canthaxanthin and echinenone at a high proportion, and a microorganism producing the total amount of zeaxanthin and β-cryptoxanthin at a high proportion may be wild strains naturally having such properties, but may be also obtained through mutation e.g. from the astaxanthin-producing microorganism.

According to the invention, the method for subjecting the carotenoid-producing microorganism to mutation treatment is not particularly restricted in so far as it induces mutation. For example, chemical methods employing mutagenic agents such as N-methyl-N'-nitro-N-nitrosoguanidine (NTG) and ethyl methanesulfonate (EMS), physical methods such as ultraviolet irradiation and X-ray irradiation, biological methods employing gene recombination, transposon, and the like can be used. The mutation treatment may be carried out at a time, or twice or more e.g. in the manner that the mutation treatment is performed to provide mutants of the carotenoid-producing microorganism which are further subjected to mutation treatment.

From among the mutants of the carotenoid-producing microorganism obtained as described above, a mutant strain having a higher product proportion (mass %) of β-carotene to the whole production amount of carotenoids than the parent strain is then selected to provide a β-carotene-producing microorganism. For this purpose, colonies may be formed on a solid medium after the mutation treatment, followed by randomly selecting colonies, but colonies taking on yellow to orange color are selected for efficiently picking the β-carotene-producing microorganism (mutant) because colonies of the β-carotene-producing microorganism often take on such colors. The inclusion of this step dramatically improves a probability capable of obtaining a mutation strain having a high product proportion of β-carotene to the whole production amount of carotenoids.

The colonies of each mutant strain selected as described above may be then cultured using a conventional method, and carotenoid compounds contained in the culture solution of each mutant strain may be analyzed to select a mutant strain having a high product proportion of β-carotene.

The cultivation of the mutant strain can be carried out, for example, in a medium which is necessary for the growth of the producing microorganism and contains ingredients generating carotenoid compounds. The method for cultivation may be any method including shake culture using test tubes, flasks, or the like, aeration agitation culture, and the like. The method for analyzing the carotenoid compounds may be any method if it can separate and detect carotenoid compounds; for example, high performance liquid chromatography, thin layer chromatography, or paper chromatography may be used.

According to the present invention, the β-carotene-producing microorganism is obtained by screening for a mutant strain having a high product proportion of β-carotene based on the whole amount of carotenoids. A carotenoid-producing microorganism like the E-396 strain concurrently produces many kinds of carotenoid compounds such as astaxanthin, canthaxanthin, adonixanthin, β-carotene, echinenone, zeaxanthin, β-cryptoxanthin, 3-hydroxyechinenone, asteroidenone, and adonirubin. Thus, the product proportion of β-carotene based on the whole amount of carotenoids is low, being usually on the order of 0 to 20 mass %.

According to the invention, mutation is induced in the carotenoid-producing microorganism, followed by screening for a mutant strain having a particularly high product proportion of β-carotene to the whole production amount of carotenoids. Criteria for the selection at least require that the product proportion of β-carotene in the mutant strain is higher than that of β-carotene in the parent strain; there is selected a mutant strain in which the product proportion of β-carotene to the whole production amount of carotenoids is preferably 50 mass % or more, more preferably 70 mass % or more, and even more preferably 90 mass % or more.

It is estimated that the biosynthesis of carotenoids, as described above, takes place by modifying the 6-membered rings at both ends thereof using an enzyme for ketonization and a hydroxylase, respectively to produce canthaxanthin, zeaxanthin, astaxanthin, and the like (See FIG. 1). Complete deficiency of the enzyme for ketonization and the hydroxylase is estimated to lead to the production of only compounds up to β-carotene and to provide no production of echinenone, β-cryptoxanthin, 3-hydroxyechinenone, asteroidenone, canthaxanthin, zeaxanthin, adonirubin, adonixanthin, and astaxanthin subsequent to β-carotene. Incomplete deficiency of the enzyme for ketonization and the hydroxylase is estimated to increase the product proportion of β-carotene and to produce decreased proportions of echinenone, β-cryptoxanthin, 3-hydroxyechinenone, asteroidenone, canthaxanthin, zeaxanthin, adonirubin, adonixanthin, and astaxanthin based on the whole amount of carotenoids. Thus, as another useful means for selecting the β-carotene-producing microorganism from among the mutant strains, a method can be used in which the selection is carried out on the basis of decreased proportions of echinenone, β-cryptoxanthin, 3-hydroxyechinenone, asteroidenone, canthaxanthin, zeaxanthin, adonirubin, adonixanthin, and astaxanthin based on the whole amount of carotenoids. The selection may be performed based on that the proportion of each of the above-described compounds to the total carotenoids is less than 20 mass %, preferably less than 10 mass %, and more preferably less than 5 mass %.

Mutation treatment of a carotenoid-producing microorganism and selection of a lycopene-producing mutant strain The parent strain for mutation used in the invention is defined as a carotenoid-producing microorganism in which the base sequence of DNA corresponding to 16S ribosomal RNA has 98% or more homology to the base sequence described in SEQ ID NO: 1 and which produces at least one carotenoid compound selected from β-carotene, echinenone, β-cryptoxanthin, 3-hydroxyechinenone, asteroidenone, canthaxanthin, zeaxanthin, adonirubin, adonixanthin, and astaxanthin. A wild strain producing at least one of the above-described carotenoids may be used as the parent strain for mutation, but a mutant strain having the productivity of astaxanthin, canthaxanthin, zeaxanthin, β-carotene, or the like improved by artificial mutation treatment can be also employed as the parent strain.

According to the invention, a method for subjecting the carotenoid-producing microorganism to mutation treatment is not particularly restricted in so far as it induces mutation. For example, chemical methods employing mutagenic agents such as N-methyl-N'-nitro-N-nitrosoguanidine (NTG) and ethyl methanesulfonate (EMS), physical methods such as ultraviolet irradiation and X-ray irradiation, biological methods employing gene recombination, transposon, and the like can be used. The mutation treatment may be carried out at a time, or twice or more e.g. in the manner that the mutation treatment is performed to provide mutants of the carotenoid-producing microorganism which are further subjected to mutation treatment.

From among the mutants of the carotenoid-producing microorganism obtained as described above, a mutant strain having a higher product proportion (mass %) of lycopene to the whole production amount of carotenoids than the parent strain is then selected to provide the lycopene-producing microorganism. For this purpose, colonies may be formed on a solid medium after the mutation treatment, followed by randomly selecting colonies, but colonies taking on pink to reddish violet are selected in comparison with red to tango color colonies of the parent strain for efficiently picking the lycopene-producing microorganism (mutant) because colonies of the lycopene-producing microorganism often take on pink to reddish violet. The inclusion of this step dramatically improves a probability capable of obtaining a mutation strain having a high product proportion of lycopene to the whole production amount of carotenoids.

The colonies of each mutant strain selected as described above may be then cultured using a conventional method, and carotenoid compounds contained in the culture solution of each mutant strain may be analyzed to select a mutant strain having a high product proportion of lycopene.

The cultivation of the mutant strain can be carried out, for example, in a medium which is necessary for the growth of the producing microorganism and contains ingredients generating carotenoid compounds. The method for cultivation may be any method including shake culture using test tubes, flasks, or the like, aeration agitation culture, and the like. The method for analyzing the carotenoid compounds may be any method if it can separate and detect carotenoid compounds; for example, high performance liquid chromatography, thin layer chromatography, or paper chromatography may be used.

According to the present invention, the lycopene-producing microorganism is obtained by screening for a mutant strain having a high product proportion of lycopene to the whole production amount of carotenoids; "the whole amount of carotenoids" as used herein refers to the total amount of carotenoids such as lycopene, β-carotene, echinenone, β-cryptoxanthin, 3-hydroxyechinenone, asteroidenone, canthaxanthin, zeaxanthin, adonirubin, adonixanthin, and astaxanthin.

A carotenoid-producing microorganism like the E-396 strain concurrently produces many kinds of carotenoid compounds such as astaxanthin, canthaxanthin, adonixanthin, β-carotene, echinenone, zeaxanthin, β-cryptoxanthin, 3-hydroxyechinenone, asteroidenone, and adonirubin. Thus, the product proportion of lycopene to the whole production amount of carotenoids is low, being usually on the order of 0 to 5 mass %.

According to the invention, mutation is induced in a carotenoid-producing microorganism, followed by screening for a mutant strain having a particularly high product proportion of lycopene to the whole production amount of carotenoids. Criteria for the selection at least require that the product proportion of lycopene in the mutant strain is higher than that of lycopene in the parent strain; there is selected a mutant strain in which the product proportion of lycopene to the whole production amount of carotenoids is preferably 40 mass % or more, more preferably 65 mass % or more, and even more preferably 90 mass % or more.

It is estimated that the biosynthesis of carotenoids takes place by forming rings at both ends of lycopene to generate β-carotene whose 6-membered rings at both ends are further modified by an enzyme for ketonization and a hydroxylase, respectively to produce canthaxanthin, zeaxanthin, astaxanthin, and the like (See FIG. 1). Complete deficiency of the cyclase is estimated to lead to the production of only lycopene and to provide no production of β-carotene, echinenone, β-cryptoxanthin, 3-hydroxyechinenone, asteroidenone, canthaxanthin, zeaxanthin, adonirubin, adonixanthin, and astaxanthin subsequent to lycopene. Incomplete deficiency of the cyclase is estimated to increase the product proportion of lycopene and to produce decreased proportions of β-carotene, echinenone, β-cryptoxanthin, 3-hydroxyechinenone, asteroidenone, canthaxanthin, zeaxanthin, adonirubin, adonixanthin, and astaxanthin based on the whole amount of carotenoids. Thus, as another useful means for selecting the lycopene-producing microorganism from among the mutant strains, a method can be used in which the selection is carried out on the basis of decreased proportions of β-carotene, echinenone, β-cryptoxanthin, 3-hydroxyechinenone, asteroidenone, canthaxanthin, zeaxanthin, adonirubin, adonixanthin, and astaxanthin based on the whole amount of carotenoids. The selection may be performed based on that the proportion of each of the above-described compounds to the total carotenoids is less than 20 mass %, preferably less than 10 mass %, and more preferably less than 5 mass %.

Culturing the selected mutant strains and harvesting carotenoid compounds

Then, the zeaxanthin-producing mutant strain, β-carotene-producing mutant strain, or lycopene-producing mutant strain selected as described above is cultured as stated below, followed by harvesting a desired carotenoid compound.

According to the invention, each of the above-described mutant microorganisms is cultured in order to harvest zeaxanthin, β-carotene, lycopene, or a carotenoid mixture containing the same. The method for culturing such mutant microorganisms may be any method, provided that desired carotenoid compounds are produced, however the following methods can be employed. That is, the medium uses that containing a carbon source, a nitrogen source, inorganic salts, and, if necessary, particular demand substances (e.g. vitamins, amino acids, nucleic acids, and the like) which are required for the growth of the producing microorganism. Examples of the carbon source include saccharides such as glucose, sucrose, fructose, trehalose, mannose, mannitol, and maltose, organic acids such as acetic acid, fumaric acid, citric acid, propionic acid, malic acid, and malonic acid, alcohols such as ethanol, propanol, butanol, pentanol, hexanol, and isobutanol, and the like. The addition proportion varies, depending on the type of carbon source used, but is typically 1 to 100 g, preferably 2 to 50 g per L of the medium. Examples of the nitrogen source used include one or more selected from a group consisting of potassium nitrate, ammonium nitrate, ammonium chloride, ammonium sulfate, ammonium phosphate, ammonia, urea, monosodium glutamate and the like. The addition proportion varies, depending on the type of nitrogen source used, but is typically 0.1 to 20 g, preferably 1 to 10 g per L of the medium. Examples of the inorganic salt used include one or more kinds from potassium dihydrogenphosphate, dipotassium hydrogen phosphate, disodium hydrogenphosphate, magnesium sulfate, magnesium chloride, iron sulfate, iron chloride, manganese sulfate, manganese chloride, zinc sulfate, zinc chloride, copper sulfate, calcium chloride, calcium carbonate, and sodium carbonate. The addition proportion varies, depending on the type of inorganic salt used, but is typically 0.1 mg to 10 g per L of the medium. Examples of the particular demand substance used include one or more kinds from vitamins, nucleic acids, yeast extract, peptone, meat extract, malt extract, corn steep liquor, dried yeast, soybean waste, soya bean oil, olive oil, corn oil, and linseed oil. The addition proportion varies, depending on the type of particular demand substance, but is typically 0.01 mg to 100 g per L of the medium. The pH of the medium is adjusted to 2 to 12, preferably 6 to 9. The culture condition comprises a temperature of 10 to 70° C., preferably 20 to 35° C.; shake culture or aeration agitation culture is typically conducted for 1 to 20 days, preferably 2 to 9 days.

Then, an operation to remove water from the culture solution obtained as described above is carried out. It depends on conditions such as the coloring matter content of the culture solution to what extent water should be removed from the culture solution in order to obtain zeaxanthin, β-carotene, lycopene, or a carotenoid mixture containing the same, but typically, filtration operation is first carried out and, if further removal of water is necessary, the precipitate is dried. The method for filtration can be performed using conventional filtration or centrifugation, or the like. If further removal of water is necessary, a method for drying the precipitate can be adopted. Examples of the drying method include, for example, conventional spray drying, drum drying, and freeze-drying.

The content of a desired carotenoid compound can be optionally increased by extraction. A raw material for extraction may use the culture solution itself, or may employ the precipitate after filtration or the dried matter thereof Examples of the extracting method include, for example, solvent extraction and supercritical carbon dioxide extraction. An organic solvent as used for the extraction is not particularly restricted, and may be a water-soluble organic solvent or a water-insoluble organic solvent. Examples of the water-soluble organic solvent include tetrahydrofuran, pyridine, dioxane, cyclohexane, cyclohexanol, methanol, ethanol, isopropanol, acetone, ethyl methyl ketone, dimethylformamide, and dimethylsulfoxide. Extraction solvents may be used as a mixture of two kinds or more, or by mixing with water. The resultant extract can be subjected to vacuum concentration or the like to remove the solvent to make a product. Optionally, deodorization treatment or suspension in vegetable oil may be carried out.

When the content of a desired carotenoid compound is required to be further increased, it is recommended that purification is performed using conventional purification means including liquid-liquid extraction employing a combination of two or more kinds of solvents and column chromatography, followed by concentrating or cooling an extract or an eluate or the like containing the carotenoid compound, or adding a poor solvent to precipitate the carotenoid compound.

Culture precipitates, dried precipitates, extracts, purified extracts, and the like containing the zeaxanthin, β-carotene, or lycopene, obtained by these methods can be used e.g. as compounding ingredients for feed, food materials, cosmetic materials, and pharmaceutical materials.

The present specification encompasses the contents of the specifications of Japanese Patent Application Nos. 2003-325104, 2003-325130, and 2003-325144 on which the priority of the present application is based.

BRIEF DESCRIPTION OF THE DRAWINGS

FIG. 2 is a listing of SEQ ID No: 1, (DNA of E-396(FERM E-4283), and of SEQ ID No. 2 (DNA of A-58 1-1(FERM BP-4671).

BEST MODE FOR CARRYING OUT THE INVENTION

EXAMPLES

Figure 1:
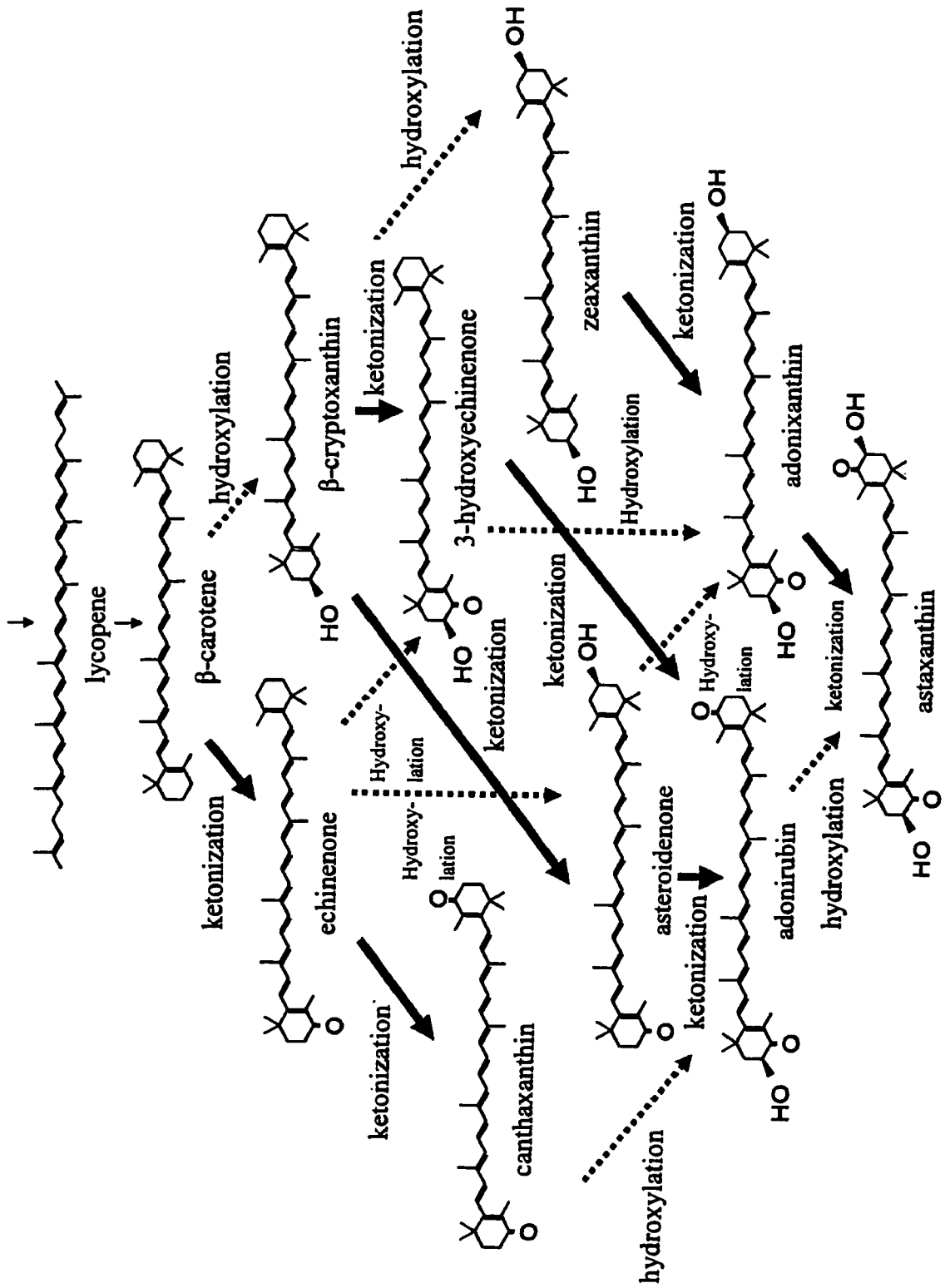
FIG. 1 is a diagram showing the biosynthetic pathway of carotenoid compounds.

The present invention is described below in further detail, based on Examples. However, the invention is not intended to be limited to only these Examples.

Example 1

A strain, E-396, (FERM BP-4283) was subjected to mutation treatment with 200 mg/L of NTG (N-methyl-N'-nitro-N-nitrosoguanidine) under standing at a temperature of 28° C. for 30 minutes. In a test tube with an inner diameter of 18 mm was placed 6 ml of a medium comprising the composition shown in Table 1 which was then subjected to steam sterilization at 121° C. for 15 minutes to make a test tube medium. There were selected 200 mutant colonies taking on yellow to orange color, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain having a 60 mass % or more product proportion of zeaxanthin to the whole production amount of carotenoids. The results of analyzing carotenoid compounds contained in this strain are shown in Table 2. For comparison purposes, the results of analyzing carotenoid compounds in a culture solution in which the E-396 strain was cultured under the same conditions as those described above are shown in Table 3.

TABLE 1

| Composition | Added amount (g/L) |
| --- | --- |
| yeast extract | 20 |
| peptone | 5 |
| sucrose | 50 |
| $KH_2PO_4$ | 1.5 |
| $Na_2HPO_4 \cdot 12H_2O$ | 3.8 |
| $MgSO_4 \cdot 7H_2O$ | 0.5 |
| $FeSO_4 \cdot 7H_2O$ | 0.01 |
| $CaCl_2 \cdot 2H_2O$ | 0.01 |
| $Na_2CO_3$ | an amount at which the medium becomes pH 7 |

TABLE 2

| Carotenoid compound | Product concentration per unit volume of culture (mg/L) | Proportion of product (mass %) |
| --- | --- | --- |
| β-carotene | 4.0 | 23.5 |
| echinenone | — | |
| 3-hydroxyechinenone | — | |
| canthaxanthin | — | |
| adonirubin | — | |
| β-cryptoxanthin | 2.4 | 14.1 |
| astaxanthin | — | |
| asteroidenone | — | |
| adonixanthin | — | |
| zeaxanthin | 10.6 | 62.4 |

"—" shows below the detection limit (0.1 mg/L).

TABLE 3

| Carotenoid compound | Product concentration per unit volume of culture (mg/L) | Proportion of product (mass %) |
| --- | --- | --- |
| β-carotene | 1.6 | 6.6 |
| echinenone | 1.8 | 7.4 |
| 3-hydroxyechinenone | 0.4 | 1.6 |
| canthaxanthin | 1.6 | 6.6 |
| adonirubin | 1.0 | 4.1 |
| β-cryptoxanthin | — | |
| astaxanthin | 6.4 | 26.3 |
| asteroidenone | 1.5 | 6.2 |
| adonixanthin | 8.6 | 35.4 |
| zeaxanthin | 1.4 | 5.8 |

"—" shows below the detection limit (0.1 mg/L).

Example 2

A strain, E-396 (FERM BP-4283), was subjected to mutation treatment with 200 mg/L of NTG (N-methyl-N'-nitro-N-nitrosoguanidine) under standing at a temperature of 28° C. for 30 minutes. In a test tube with an inner diameter of 18 mm was placed 6 ml of a medium comprising the composition shown in Table 1 which was then subjected to steam sterilization at 121° C. for 15 minutes to make a test tube medium. There were randomly selected 1,500 mutant colonies, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain being less than 10 mass % in the product proportion of each of the produced echinenone, canthaxanthin, 3-hydroxyechinenone, asteroidenone, adonirubin, adonixanthin, and astaxanthin to the whole production amount of carotenoids. The results of analyzing carotenoid compounds in this strain are shown in Table 4.

TABLE 4

| Carotenoid compound | Product concentration per unit volume of culture (mg/L) | Proportion of product (mass %) |
| --- | --- | --- |
| β-carotene | 4.4 | 31.9 |
| echinenone | — | |
| 3-hydroxyechinenone | — | |
| canthaxanthin | — | |
| adonirubin | 0.2 | 1.4 |
| β-cryptoxanthin | 3.1 | 22.5 |
| astaxanthin | 0.5 | 3.6 |
| asteroidenone | — | |
| adonixanthin | 1.1 | 8.0 |
| zeaxanthin | 4.5 | 32.6 |

"—" shows below the detection limit (0.1 mg/L).

Example 3

A strain, E-396 (FERM BP-4283), was subjected to mutation treatment with NTG, followed by selecting colonies having a deep color tone of red to provide a mutant strain, Y-559, having an improved productivity of astaxanthin. The Y-559 strain was further subjected to mutation treatment with 150 mg/L of NTG. In a test tube with an inner diameter of 18 mm was placed 6 ml of a medium comprising the composition shown in Table 1 which was then subjected to steam sterilization at 121° C. for 15 minutes to make a test tube medium. There were selected 350 mutant colonies taking on yellow to orange color, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain being less than 1% in the product proportion of each of echinenone, canthaxanthin, 3-hydroxyechinenone, asteroidenone, adonirubin, adonixanthin, and astaxanthin to the whole production amount of carotenoids. The results of analyzing carotenoid compounds in this strain are shown in Table 5. For comparison purposes, the results of analyzing carotenoid compounds in a culture solution in which the Y-559 strain was cultured under the same conditions as those described above are shown in Table 6.

TABLE 5

| Carotenoid compound | Product concentration per unit volume of culture (mg/L) | Proportion of product (mass %) |
|---|---|---|
| β-carotene | 34.0 | 59.1 |
| echinenone | — | |
| 3-hydroxyechinenone | — | |
| canthaxanthin | — | |
| adonirubin | — | |
| β-cryptoxanthin | 3.4 | 5.9 |
| astaxanthin | — | |
| asteroidenone | — | |
| adonixanthin | 0.4 | 0.7 |
| zeaxanthin | 19.7 | 34.3 |

"—" shows below the detection limit (0.1 mg/L).

TABLE 6

| Carotenoid compound | Product concentration per unit volume of culture (mg/L) | Proportion of product (mass %) |
|---|---|---|
| β-carotene | 26.2 | 13.6 |
| echinenone | 7.9 | 4.1 |
| 3-hydroxyechinenone | 0.9 | 0.5 |
| canthaxanthin | 12.0 | 6.3 |
| adonirubin | 20.3 | 10.6 |
| β-cryptoxanthin | — | |
| astaxanthin | 67.7 | 35.3 |
| asteroidenone | — | |
| adonixanthin | 56.4 | 29.4 |
| zeaxanthin | 0.6 | 0.3 |

"—" shows below the detection limit (0.1 mg/L).

Example 4

A strain, A-581-1 (FERM BP-4671) was subjected to mutation treatment with ultraviolet irradiation using a UV ramp. In a test tube with an inner diameter of 18 mm was placed 6 ml of a medium comprising the composition shown in Table 1 which was then subjected to steam sterilization at 121° C. for 15 minutes to make a test tube medium. There were selected 280 mutant colonies taking on yellow to orange color, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain having a 20 mass % or more product proportion of zeaxanthin to the whole production amount of carotenoids. The results of analyzing carotenoid compounds in this strain are shown in Table 7. For comparison purposes, the results of analyzing carotenoid compounds in a culture solution in which the A-581-1 strain was cultured under the same conditions as those described above are shown in Table 8.

TABLE 7

| Carotenoid compound | Product concentration per unit volume of culture (mg/L) | Proportion of product (mass %) |
|---|---|---|
| β-carotene | 3.9 | 48.1 |
| echinenone | — | |
| 3-hydroxyechinenone | — | |
| canthaxanthin | — | |
| adonirubin | — | |
| β-cryptoxanthin | 2.2 | 27.2 |
| astaxanthin | — | |
| asteroidenone | — | |
| adonixanthin | — | |
| zeaxanthin | 2.0 | 24.7 |

"—" shows below the detection limit (0.1 mg/L).

TABLE 8

| Carotenoid compound | Product concentration per unit volume of culture (mg/L) | Proportion of product (mass %) |
|---|---|---|
| β-carotene | 0.6 | 7.8 |
| echinenone | 0.6 | 7.8 |
| 3-hydroxyechinenone | — | |
| canthaxanthin | 0.7 | 9.1 |
| adonirubin | 0.4 | 5.2 |
| β-cryptoxanthin | — | |
| astaxanthin | 1.8 | 23.4 |
| asteroidenone | 0.4 | 5.2 |
| adonixanthin | 2.7 | 35.1 |
| zeaxanthin | 0.5 | 6.5 |

"—" shows below the detection limit (0.1 mg/L).

Example 5

A strain, E-396 (FERM BP-4283), was subjected to mutation treatment with 100 mg/L of NTG (N-methyl-N'-nitro-N-nitrosoguanidine) under standing at a temperature of 28° C. for 30 minutes. In a test tube with an inner diameter of 18 mm was placed 6 ml of a medium comprising the composition shown in Table 9 which was then subjected to steam sterilization at 121° C. for 15 minutes to make a test tube medium. There were selected 4,000 mutant colonies taking on yellow to orange color, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain having a 50 mass % or more product proportion of β-carotene to the whole production amount of carotenoids. The results of analyzing carotenoid compounds in this strain are shown in Table 10. For comparison purposes, the results of analyzing carotenoid compounds in a culture solution in which the E-396 strain was cultured under the same conditions as those described above are shown in Table 11.

TABLE 9

| Composition | Added amount (g/L) |
| --- | --- |
| yeast extract | 20 |
| peptone | 5 |
| sucrose | 50 |
| $KH_2PO_4$ | 1.5 |
| $Na_2HPO_4 \cdot 12H_2O$ | 3.8 |
| $MgSO_4 \cdot 7H_2O$ | 0.5 |
| $FeSO_4 \cdot 7H_2O$ | 0.01 |
| $CaCl_2 \cdot 2H_2O$ | 0.01 |
| $Na_2CO_3$ | an amount at which the medium becomes pH 7 |

TABLE 10

| Carotenoid compound | Product concentration per unit volume of culture (mg/L) | Proportion of product (mass %) |
| --- | --- | --- |
| β-carotene | 11.9 | 85.0 |
| echinenone | 0.2 | 1.4 |
| 3-hydroxyechinenone | — | |
| canthaxanthin | 0.3 | 2.1 |
| adonirubin | 0.4 | 2.9 |
| β-cryptoxanthin | — | |
| astaxanthin | 0.7 | 5.0 |
| asteroidenone | — | |
| adonixanthin | 0.5 | 3.6 |
| zeaxanthin | — | |

"—" shows below the detection limit (0.1 mg/L).

TABLE 11

| Carotenoid compound | Product concentration per unit volume of culture (mg/L) | Proportion of product (mass %) |
| --- | --- | --- |
| β-carotene | 1.6 | 6.6 |
| echinenone | 1.8 | 7.4 |
| 3-hydroxyechinenone | 0.4 | 1.6 |
| canthaxanthin | 1.6 | 6.6 |
| adonirubin | 1.0 | 4.1 |
| β-cryptoxanthin | — | |
| astaxanthin | 6.4 | 26.3 |
| asteroidenone | 1.5 | 6.2 |
| adonixanthin | 8.6 | 35.4 |
| zeaxanthin | 1.4 | 5.8 |

"—" shows below the detection limit (0.1 mg/L).

Example 6

A strain, E-396 (FERM BP-4283), was subjected to mutation treatment with NTG, followed by selecting orange color colonies to provide a mutant strain, CA-22, having an improved productivity of canthaxanthin. The CA-22 strain was further subjected to mutation treatment with 200 mg/L of NTG. In a test tube with an inner diameter of 18 mm was placed 6 ml of a medium comprising the composition shown in Table 9 which was then subjected to steam sterilization at 121° C. for 15 minutes to make a test tube medium. There were selected 80 mutant colonies taking on yellow to orange color, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain having a 50 mass % or more product proportion of β-carotene to the whole production amount of carotenoids. The results of analyzing carotenoid compounds in this strain are shown in Table 12. For comparison purposes, the results of analyzing carotenoid compounds in the CA-22 strain which was cultured under the same conditions as those described above are shown in Table 13.

TABLE 12

| Carotenoid compound | Product concentration per unit volume of culture (mg/L) | Proportion of product (mass %) |
| --- | --- | --- |
| β-carotene | 17.4 | 96.1 |
| echinenone | 0.4 | 2.2 |
| 3-hydroxyechinenone | — | |
| canthaxanthin | 0.3 | 1.7 |
| adonirubin | — | |
| β-cryptoxanthin | — | |
| astaxanthin | — | |
| asteroidenone | — | |
| adonixanthin | — | |
| zeaxanthin | — | |

"—" shows below the detection limit (0.1 mg/L).

TABLE 13

| Carotenoid compound | Product concentration per unit volume of culture (mg/L) | Proportion of product (mass %) |
| --- | --- | --- |
| β-carotene | 1.2 | 5.7 |
| echinenone | 2.5 | 11.9 |
| 3-hydroxyechinenone | — | |
| canthaxanthin | 16.1 | 76.7 |
| adonirubin | 0.9 | 4.3 |
| β-cryptoxanthin | — | |
| astaxanthin | 0.3 | 1.4 |
| asteroidenone | — | |
| adonixanthin | — | |
| zeaxanthin | — | |

"—" shows below the detection limit (0.1 mg/L).

Example 7

A strain, E-396 (FERM BP-4283), was subjected to mutation treatment with NTG, followed by selecting yellow colonies to provide a mutant strain, ZE-7, having an improved productivity of zeaxanthin. The ZE-7 strain was further subjected to mutation treatment with 150 mg/L of NTG. In a test tube with an inner diameter of 18 mm was placed 6 ml of a medium comprising the composition shown in Table 9 which was then subjected to steam sterilization at 121° C. for 15 minutes to make a test tube medium. There were selected 60 mutant colonies taking on yellow to orange color, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain having a 50 mass % or more product proportion of β-carotene to the whole production amount of carotenoids. The results of analyzing carotenoid compounds in this strain are shown in Table 14. For comparison purposes, the results of analyzing carotenoid compounds in the ZE-7 strain which was cultured under the same conditions as those described above are shown in Table 15.

TABLE 14

| Carotenoid compound | Product concentration per unit volume of culture (mg/L) | Proportion of product (mass %) |
|---|---|---|
| β-carotene | 16.0 | 100 |
| echinenone | — | |
| 3-hydroxyechinenone | — | |
| canthaxanthin | — | |
| adonirubin | — | |
| β-cryptoxanthin | — | |
| astaxanthin | — | |
| asteroidenone | — | |
| adonixanthin | — | |
| zeaxanthin | — | |

"—" shows below the detection limit (0.1 mg/L).

TABLE 15

| Carotenoid compound | Product concentration per unit volume of culture (mg/L) | Proportion of product (mass %) |
|---|---|---|
| β-carotene | 4.0 | 23.5 |
| echinenone | — | |
| 3-hydroxyechinenone | — | |
| canthaxanthin | — | |
| adonirubin | — | |
| β-cryptoxanthin | 2.4 | 14.1 |
| astaxanthin | — | |
| asteroidenone | — | |
| adonixanthin | — | |
| zeaxanthin | 10.6 | 62.4 |

"—" shows below the detection limit (0.1 mg/L).

Example 8

A strain, A-581-1 (FERM BP-4671) was subjected to mutation treatment with ultraviolet irradiation using a UV ramp. In a test tube with an inner diameter of 18 mm was placed 6 ml of a medium comprising the composition shown in Table 9 which was then subjected to steam sterilization at 121° C. for 15 minutes to make a test tube medium. There were selected 3,000 mutant colonies taking on yellow, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain being less than 20 mass % in the product proportion of each of echinenone, β-cryptoxanthin, 3-hydroxyechinenone, asteroidenone, canthaxanthin, zeaxanthin, adonirubin, adonixanthin, and astaxanthin to the whole production amount of carotenoids. The results of analyzing carotenoid compounds in this strain are shown in Table 16. For comparison purposes, the results of analyzing carotenoid compounds in a culture solution in which the A-581-1 strain was cultured under the same conditions as those described above are shown in Table 17.

TABLE 16

| Carotenoid compound | Product concentration per unit volume of culture (mg/L) | Proportion of product (mass %) |
|---|---|---|
| β-carotene | 2.9 | 64.4 |
| echinenone | 0.5 | 11.1 |
| 3-hydroxyechinenone | — | |
| canthaxanthin | 0.2 | 4.4 |
| adonirubin | 0.2 | 4.4 |
| β-cryptoxanthin | 0.3 | 6.7 |
| astaxanthin | 0.2 | 4.4 |
| asteroidenone | — | |
| adonixanthin | 0.2 | 4.4 |
| zeaxanthin | — | |

"—" shows below the detection limit (0.1 mg/L).

TABLE 17

| Carotenoid compound | Product concentration per unit volume of culture (mg/L) | Proportion of product (mass %) |
|---|---|---|
| β-carotene | 0.6 | 7.8 |
| echinenone | 0.6 | 7.8 |
| 3-hydroxyechinenone | — | |
| canthaxanthin | 0.7 | 9.1 |
| adonirubin | 0.4 | 5.2 |
| β-cryptoxanthin | — | |
| astaxanthin | 1.8 | 23.4 |
| asteroidenone | 0.4 | 5.2 |
| adonixanthin | 2.7 | 35.1 |
| zeaxanthin | 0.5 | 6.5 |

"—" shows below the detection limit (0.1 mg/L).

Example 9

A strain, E-396 (FERM BP-4283), was subjected to mutation treatment with 100 mg/L of NTG (N-methyl-N'-nitro-N-nitrosoguanidine) under standing at a temperature of 28° C. for 30 minutes. In a test tube with an inner diameter of 18 mm was placed 6 ml of a medium comprising the composition shown in Table 18 which was then subjected to steam sterilization at 121° C. for 15 minutes to make a test tube medium. There were selected 60 mutant colonies taking on pink to reddish violet, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain having a 40 mass % or more product proportion of lycopene to the whole production amount of carotenoids. The results of analyzing carotenoid compounds in this strain are shown in Table 19. For comparison purposes, the results of analyzing carotenoid compounds in a culture solution in which the E-396 strain was cultured under the same conditions as those described above are shown in Table 20.

TABLE 18

| Composition | Added amount (g/L) |
|---|---|
| yeast extract | 20 |
| peptone | 5 |
| sucrose | 50 |
| $KH_2PO_4$ | 1.5 |
| $Na_2HPO_4 \cdot 12H_2O$ | 3.8 |
| $MgSO_4 \cdot 7H_2O$ | 0.5 |
| $FeSO_4 \cdot 7H_2O$ | 0.01 |

TABLE 18-continued

| Composition | Added amount (g/L) |
| --- | --- |
| CaCl$_2$•2H$_2$O | 0.01 |
| Na$_2$CO$_3$ | an amount at which the medium becomes pH 7 |

TABLE 19

| Carotenoid compound | Product concentration per unit volume of culture (mg/L) | Proportion of product (mass %) |
| --- | --- | --- |
| lycopene | 15.5 | 96.3 |
| β-carotene | — | |
| echinenone | — | |
| 3-hydroxyechinenone | — | |
| canthaxanthin | — | |
| adonirubin | — | |
| β-cryptoxanthin | — | |
| astaxanthin | 0.3 | 1.9 |
| asteroidenone | — | |
| adonixanthin | 0.3 | 1.9 |
| zeaxanthin | — | |

"—" shows below the detection limit (0.1 mg/L).

TABLE 20

| Carotenoid compound | Product concentration per unit volume of culture (mg/L) | Proportion of product (mass %) |
| --- | --- | --- |
| lycopene | — | |
| β-carotene | 1.6 | 6.6 |
| echinenone | 1.8 | 7.4 |
| 3-hydroxyechinenone | 0.4 | 1.6 |
| canthaxanthin | 1.6 | 6.6 |
| adonirubin | 1.0 | 4.1 |
| β-cryptoxanthin | — | |
| astaxanthin | 6.4 | 26.3 |
| asteroidenone | 1.5 | 6.2 |
| adonixanthin | 8.6 | 35.4 |
| zeaxanthin | 1.4 | 5.8 |

"—" shows below the detection limit (0.1 mg/L).

Example 10

A strain, E-396 (FERM BP-4283), was subjected to mutation treatment with 100 mg/L of NTG (N-methyl-N'-nitro-N-nitrosoguanidine) under standing at a temperature of 28° C. for 30 minutes. In a test tube with an inner diameter of 18 mm was placed 6 ml of a medium comprising the composition shown in Table 18 which was then subjected to steam sterilization at 121° C. for 15 minutes to make a test tube medium. There were randomly selected 800 mutant colonies, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain having a 40 mass % or more product proportion of lycopene to the whole production amount of carotenoids. The results of analyzing carotenoid compounds in this strain are shown in Table 21. For comparison purposes, the results of analyzing carotenoid compounds in a culture solution in which the E-396 strain was cultured under the same conditions as those described above are shown in Table 20.

TABLE 21

| Carotenoid compound | Product concentration per unit volume of culture (mg/L) | Proportion of product (mass %) |
| --- | --- | --- |
| lycopene | 10.1 | 74.3 |
| β-carotene | 0.2 | 1.5 |
| echinenone | 0.5 | 3.7 |
| 3-hydroxyechinenone | — | |
| canthaxanthin | 0.3 | 2.2 |
| adonirubin | 0.4 | 2.9 |
| β-cryptoxanthin | — | |
| astaxanthin | 1.2 | 8.8 |
| asteroidenone | — | |
| adonixanthin | 0.9 | 6.6 |
| zeaxanthin | — | |

"—" shows below the detection limit (0.1 mg/L).

Example 11

A strain, E-396 (FERM BP-4283), was subjected to mutation treatment with NTG, followed by selecting colonies having a deep color tone of red to provide a mutant strain, Y-559, having an improved productivity of astaxanthin. The Y-559 strain was further subjected to mutation treatment with 150 mg/L of NTG. In a test tube with an inner diameter of 18 mm was placed 6 ml of a medium comprising the composition shown in Table 18 which was then subjected to steam sterilization at 121° C. for 15 minutes to make a test tube medium. There were selected 80 mutant colonies taking on pink to reddish violet, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain having a 40 mass % or more product proportion of lycopene to the whole production amount of carotenoids. The results of analyzing carotenoid compounds in this strain are shown in Table 22. For comparison purposes, the results of analyzing carotenoid compounds in a culture solution in which the Y-559 strain was cultured under the same conditions as those described above are shown in Table 23.

TABLE 22

| Carotenoid compound | Product concentration per unit volume of culture (mg/L) | Proportion of product (mass %) |
| --- | --- | --- |
| lycopene | 163.9 | 99.6 |
| β-carotene | — | |
| echinenone | — | |
| 3-hydroxyechinenone | — | |
| canthaxanthin | — | |
| adonirubin | — | |
| β-cryptoxanthin | — | |
| astaxanthin | 0.7 | 0.4 |
| asteroidenone | — | |
| adonixanthin | — | |
| zeaxanthin | — | |

"—" shows below the detection limit (0.1 mg/L).

TABLE 23

| Carotenoid compound | Product concentration per unit volume of culture (mg/L) | Proportion of product (mass %) |
|---|---|---|
| lycopene | — | |
| β-carotene | 26.2 | 13.6 |
| echinenone | 7.9 | 4.1 |
| 3-hydroxyechinenone | 0.9 | 0.5 |
| canthaxanthin | 12.0 | 6.3 |
| adonirubin | 20.3 | 10.6 |
| β-cryptoxanthin | — | |
| astaxanthin | 67.7 | 35.3 |
| asteroidenone | — | |
| adonixanthin | 56.4 | 29.4 |
| zeaxanthin | 0.6 | 0.3 |

"—" shows below the detection limit (0.1 mg/L)

Example 12

A strain, E-396 (FERM BP-4283), was subjected to mutation treatment with NTG, followed by selecting orange color colonies to provide a mutant strain, CA-22, having an improved productivity of canthaxanthin. The CA-22 strain was further subjected to mutation treatment with 200 mg/L of NTG. In a test tube with an inner diameter of 18 mm was placed 6 ml of a medium comprising the composition shown in Table 18 which was then subjected to steam sterilization at 121° C. for 15 minutes to make a test tube medium. There were selected 60 mutant colonies taking on pink to reddish violet, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain having a 40 mass % or more product proportion of lycopene to the whole production amount of carotenoids. The results of analyzing carotenoid compounds in this strain are shown in Table 24. For comparison purposes, the results of analyzing carotenoid compounds in the CA-22 strain which was cultured under the same conditions as those described above are shown in Table 25.

TABLE 24

| Carotenoid compound | Product concentration per unit volume of culture (mg/L) | Proportion of product (mass %) |
|---|---|---|
| lycopene | 19.3 | 98.0 |
| β-carotene | — | |
| echinenone | — | |
| 3-hydroxyechinenone | — | |
| canthaxanthin | 0.4 | 2.0 |
| adonirubin | — | |
| β-cryptoxanthin | — | |
| astaxanthin | — | |
| asteroidenone | — | |
| adonixanthin | — | |
| zeaxanthin | — | |

"—" shows below the detection limit (0.1 mg/L).

TABLE 25

| Carotenoid compound | Product concentration per unit volume of culture (mg/L) | Proportion of product (mass %) |
|---|---|---|
| lycopene | — | |
| β-carotene | 1.2 | 5.7 |
| echinenone | 2.5 | 11.9 |
| 3-hydroxyechinenone | — | |
| canthaxanthin | 16.1 | 76.7 |
| adonirubin | 0.9 | 4.3 |
| β-cryptoxanthin | — | |
| astaxanthin | 0.3 | 1.4 |
| asteroidenone | — | |
| adonixanthin | — | |
| zeaxanthin | — | |

"—" shows below the detection limit (0.1 mg/L).

Example 13

A strain, E-396 (FERM BP-4283), was subjected to mutation treatment with NTG, followed by selecting yellow colonies to provide a mutant strain, ZE-7, having an improved productivity of zeaxanthin. The ZE-7 strain was further subjected to mutation treatment with 150 mg/L of NTG. In a test tube with an inner diameter of 18 mm was placed 6 ml of a medium comprising the composition shown in Table 18 which was then subjected to steam sterilization at 121° C. for 15 minutes to make a test tube medium. There were selected 80 mutant colonies taking on pink to reddish violet, each of which then was, in an amount of one platinum loop, inoculated on the test tube medium and subjected to reciprocating shaken culture at 330 rpm and 28° C. for 5 days. These cultures were then subjected to centrifugal separation, followed by analyzing carotenoid compounds in the resultant cell bodies using high performance liquid chromatography, with the result of providing one strain having a 40 mass % or more product proportion of lycopene to the whole production amount of carotenoids. The results of analyzing carotenoid compounds in this strain are shown in Table 26. For comparison purposes, the results of analyzing carotenoid compounds in a culture solution in which the ZE-7 strain was cultured under the same conditions as those described above are shown in Table 27.

TABLE 26

| Carotenoid compound | Product concentration per unit volume of culture (mg/L) | Proportion of product (mass %) |
|---|---|---|
| lycopene | 17.1 | 96.1 |
| β-carotene | — | |
| echinenone | — | |
| 3-hydroxyechinenone | — | |
| canthaxanthin | — | |
| adonirubin | — | |
| β-cryptoxanthin | 0.2 | 1.1 |
| astaxanthin | — | |
| asteroidenone | — | |
| adonixanthin | — | |
| zeaxanthin | 0.5 | 2.8 |

"—" shows below the detection limit (0.1 mg/L).

TABLE 27

| Carotenoid compound | Product concentration per unit volume of culture (mg/L) | Proportion of product (mass %) |
| --- | --- | --- |
| ene | — | |
| β-carotene | 4.0 | 23.5 |
| echinenone | — | |
| 3-hydroxyechinenone | — | |
| canthaxanthin | — | |
| adonirubin | — | |
| β-cryptoxanthin | 2.4 | 14.1 |
| astaxanthin | — | |
| asteroidenone | — | |
| adonixanthin | — | |
| zeaxanthin | 10.6 | |

"—" shows below the detection limit (0.1 mg/L).

Example 14

A strain, A-581-1 (FERM BP-4671), was subjected to mutation treatment with ultraviolet irradiation using a UV ramp. In a test tube with an inner diameter of 18 mm was placed 6 ml of a medium comprising the composition shown in Table 18 which was then subjected to steam sterilization at 121° C. for 15 minutes to make a test tube medium. There were selected 100 mutant colonies taking on pink, each of which then was, in an amount of one platinum loop, inoculated on the test tube medium and subjected to reciprocating shaken culture at 330 rpm and 28° C. for 4 days. These cultures were then subjected to centrifugal separation, followed by analyzing carotenoid compounds in the resultant cell bodies using high performance liquid chromatography, with the result of providing one strain being less than 20 mass % in the product proportion of each of β-carotene, echinenone, β-cryptoxanthin, 3-hydroxyechinenone, asteroidenone, canthaxanthin, zeaxanthin, adonirubin, adonixanthin, and astaxanthin to the whole production amount of carotenoids. The results of analyzing carotenoid compounds in this strain are shown in Table 28. For comparison purposes, the results of analyzing carotenoid compounds in a culture solution in which the A-581-1 strain was cultured under the same conditions as those described above are shown in Table 29

TABLE 28

| Carotenoid compound | Product concentration per unit volume of culture (mg/L) | Proportion of product (mass %) |
| --- | --- | --- |
| lycopene | 3.3 | 54.1 |
| β-carotene | — | |
| echinenone | 0.4 | 6.6 |
| 3-hydroxyechinenone | — | |
| canthaxanthin | 0.3 | 4.9 |
| adonirubin | 0.3 | 4.9 |
| β-cryptoxanthin | — | |
| astaxanthin | 1.1 | 18.0 |
| asteroidenone | — | |
| adonixanthin | 0.7 | 11.5 |
| zeaxanthin | — | |

"—" shows below the detection limit (0.1 mg/L).

TABLE 29

| Carotenoid compound | Product concentration per unit volume of culture (mg/L) | Proportion of product (mass %) |
| --- | --- | --- |
| lycopene | — | |
| β-carotene | 0.6 | 7.8 |
| echinenone | 0.6 | 7.8 |
| 3-hydroxyechinenone | — | |
| canthaxanthin | 0.7 | 9.1 |
| adonirubin | 0.4 | 5.2 |
| β-cryptoxanthin | — | |
| astaxanthin | 1.8 | 23.4 |
| asteroidenone | 0.4 | 5.2 |
| adonixanthin | 2.7 | 35.1 |
| zeaxanthin | 0.5 | 6.5 |

"—" shows below the detection limit (0.1 mg/L).

All publications cited herein are hereby incorporated as reference in their entirety.

INDUSTRIAL APPLICABILITY

The process of the invention is useful for producing zeaxanthin, β-carotene, and lycopene and a carotenoid mixture containing the same as the main component which are useful as coloring agents, antioxidant agents, or the like.

There is provided according to the invention an inexpensive process for producing zeaxanthin, β-carotene, or lycopene with high safety by which they can be stably supplied.

According to the invention, some mutant strains producing zeaxanthin, β-carotene, or lycopene also may simultaneously produce other carotenoid compounds such as, for example, β-cryptoxanthin and/or β-carotene as by-products, together with zeaxanthin, β-carotene, or lycopene as the main product, the process of the invention being also useful as a process for efficiently producing these carotenoid mixtures.

---

SEQUENCE LISTING

```
<160> NUMBER OF SEQ ID NOS: 2

<210> SEQ ID NO 1
<211> LENGTH: 1452
<212> TYPE: DNA
<213> ORGANISM: Unknown
<220> FEATURE:
<223> OTHER INFORMATION: Description of unknown organisms : Base
      sequence of DNA of E-396(FERM BP-4283) corresponding to 16S
      ribosomal RNA
```

```
<220> FEATURE:
<221> NAME/KEY: unsure
<222> LOCATION: (1350)..(1350)
<223> OTHER INFORMATION: No. 1350 is unidentified

<400> SEQUENCE: 1
agtttgatcc tggctcagaa cgaacgctgg cggcaggctt aacacatgca agtcgagcga      60
gaccttcggg tctagcggcg gacgggtgag taacgcgtgg aacgtgccc ttctctacgg     120 aatagccccg ggaaactggg agtaataccg tatacgccct ttgggggaaa gatttatcgg    180
agaaggatcg gcccgcgttg gattaggtag ttggtgggt aatggcccac caagccgacg     240
atccatagct ggtttgagag gatgatcagc cacactggga ctgagacacg gcccagactc    300
ctacgggagg cagcagtggg gaatcttaga caatgggggc aaccctgatc tagccatgcc    360
gcgtgagtga tgaaggcctt agggttgtaa agctctttca gctgggaaga taatgacggt    420
accagcagaa gaagcccgg ctaactccgt gccagcagcc gcggtaatac ggagggggct     480
agcgttgttc ggaattactg ggcgtaaagc gcacgtaggc ggactggaaa gtcagaggtg    540
aaatcccagg gctcaaccett ggaactgcct ttgaaactat cagtctggag ttcgagagag   600
gtgagtggaa ttccgagtgt agaggtgaaa ttcgtagata ttcggaggaa caccagtggc    660
gaaggcggct cactggctcg atactgacgc tgaggtgcga aagcgtgggg agcaaacagg    720
attagatacc ctggtagtcc acgccgtaaa cgatgaatgc cagacgtcgg caagcatgct    780
tgtcggtgtc acacctaacg gattaagcat tccgcctggg gagtacggtc gcaagattaa    840
aactcaaagg aattgacggg ggcccgcaca agcggtggag catgtggttt aattcgaagc    900
aacgcgcaga accttaccaa cccttgacat ggcaggaccg ctggagagat tcagctttct    960
cgtaagagac ctgcacacag gtgctgcatg gctgtcgtca gctcgtgtcg tgagatgttc   1020
ggttaagtcc ggcaacgagc gcaacccacg tccctagttg ccagcaattc agttgggaac   1080
tctatggaaa ctgccgatga taagtcggag gaaggtgtgg atgacgtcaa gtcctcatgg   1140
gccttacggg ttgggctaca cacgtgctac aatggtggtg acagtgggtt aatccccaaa   1200
agccatctca gttcggattg tcctctgcaa ctcgagggca tgaagttgga atcgctagta   1260
atcgcggaac agcatgccgc ggtgaatacg ttcccgggcc ttgtacacac cgcccgtcac   1320
accatgggag ttggttctac ccgacgacgn tgcgctaacc ttcggggggc aggcggccac   1380
ggtaggatca gcgactgggg tgaagtcgta acaaggtagc cgtagggaa cctgcggctg    1440 gatcacctcc tt                                                       1452

<210> SEQ ID NO 2
<211> LENGTH: 1426
<212> TYPE: DNA
<213> ORGANISM: Unknown
<220> FEATURE:
<223> OTHER INFORMATION: Description of unknown organisms : Base
      sequence of DNA of A-581-1 (FERM BP-4671) corresponding to 16S
      ribosomal RNA

<400> SEQUENCE: 2
tagagtttga tcctggctca gaacgaacgc tggcggcagg cttaacacat gcaagtcgag     60
cgagaccttc gggtctagcg gcggacgggt gagtaacgcg tggaacgtg cccttctcta    120 cggaatagcc ccgggaaact gggagtaata ccgtatacgc cctttggggg aaagatttat   180
cggagaagga tcggcccgcg ttggattagg tagttggtga gtaacgct caccaagccg      240 acgatccata gctggtttga gaggatgatc agccacactg gactgagac acggcccaga    300
```

```
                                                                           -continued
ctcctacggg aggcagcagt ggggaatctt agacaatggg ggcaaccctg atctagccat          360
gccgcgtgag tgatgaaggc cttagggttg taaagctctt tcagctggga agataatgac          420
ggtaccagca gaagaagccc cggctaactc cgtgccagca gccgcggtaa tacggagggg          480
gctagcgttg ttcggaatta ctgggcgtaa agcgcacgta ggcggactgg aaagtcagag          540
gtgaaatccc agggctcaac cttggaactg cctttgaaac tatcagtctg gagttcgaga          600
gaggtgagtg gaattccgag tgtagaggtg aaattcgtag atattcggag gaacaccagt          660
ggcgaaggcg gctcactggc tcgatactga cgctgaggtg cgaaagcgtg gggagcaaac          720
aggattagat accctggtag tccacgccgt aaacgatgaa tgccagacgt cggcaagcat          780
gcttgtcggt gtcacaccta acggattaag cattccgcct ggggagtacg gtcgcaagat          840
taaaactcaa aggaattgac gggggcccgc acaagcggtg gagcatgtgg tttaattcga          900
agcaacgcgc agaaccttac caaccttga catggcagga ccgctggaga gattcagctt          960
tctcgtaaga gacctgcaca caggtgctgc atggctgtcg tcagctcgtg tcgtgagatg         1020
ttcggttaag tccggcaacg agcgcaaccc acgtccctag ttgccagcat tcagttgggc         1080
actctatgga aactgccggt gataagccgg aggaaggtgt ggatgacgtc aagtcctcat         1140
ggcccttacg ggttgggcta cacacgtgct acaatggtgg tgacagtggg ttaatcccca         1200
aaagccatct cagttcggat tgtcctctgc aactcgaggg catgaagttg gaatcgctag         1260
taatcgcgga acagcatgcc gcggtgaata cgttcccggg ccttgtacac accgcccgtc         1320
acaccatggg agttggttct acccgacgac gctgcgctaa cccttcgggg aggcaggcgg         1380
ccacggtagg atcagcgact ggggtgaagt cgtaacaagg tagcca                        1426
```

The invention claimed is:

1. A process for producing a carotenoid mixture containing zeaxanthin and β-cryptoxanthin, comprising
    mutating a parent astaxanthin-producing bacterium having a 16S ribosomal RNA that is not less than 98% homologous to sequence of SEQ ID NO: 1;
    culturing the mutants obtained to form colonies on a solid medium;
    selecting yellow to orange colonies on said solid medium;
    culturing the selected mutant colonies in a culture medium;
    extracting and analyzing the carotenoids in the culture;
    screening for a mutant strain having 20% or more proportion by mass of zeaxanthin to total carotenoids in said culture to provide a bacterium producing zeaxanthin and β-cryptoxanthin;
    culturing said bacterium; and harvesting a carotenoid mixture containing zeaxanthin and β-cryptoxanthin from the resultant culture.

2. The process according to claim 1, wherein the proportion of each of echinenone, 3-hydroxyechinenone, asteroidenone, canthaxanthin, adonirubin, adonixanthin, and astaxanthin produced by said zeaxanthin-producing microorganism is less than 10% proportion by mass to the total amount of carotenoids in the carotenoid mixture produced.

3. The process according to claim 1, wherein said carotenoid mixture containing zeaxanthin further comprises β-carotene.

4. The process according to claim 1, wherein said parent astaxanthin-producing bacterium is selected from the group consisting of strain E-396 (FERM BP-4283) and strain A-581-1 (FERM BP-4671).

* * * * *